United States Patent [19]

Billich et al.

[11] Patent Number: 5,538,997
[45] Date of Patent: Jul. 23, 1996

[54] 2,4-DIAMINO-3-HYDROXYCARBOXYLIC ACID DERIVATIVES

[75] Inventors: Andreas Billich; Brigitte Charpiot; Peter Ettmayer; Hubert Gstach, all of Vienna; Philipp Lehr, Mödling; Dieter Scholz, Vienna, all of Austria

[73] Assignee: Sandoz Ltd., Basel, Switzerland

[21] Appl. No.: 177,687

[22] Filed: Jan. 3, 1994

[30] Foreign Application Priority Data

Mar. 12, 1993 [GB] United Kingdom .................. 9305144
Sep. 23, 1993 [GB] United Kingdom .................. 9319667

[51] Int. Cl.$^6$ .......................... A61K 31/21; C07C 275/26
[52] U.S. Cl. ............................................ 514/510; 564/57
[58] Field of Search ...................... 514/506, 510; 564/57

[56] References Cited

U.S. PATENT DOCUMENTS 4,661,473  4/1987  Boger et al. .............................. 514/16

FOREIGN PATENT DOCUMENTS

| 0337714 | 10/1989 | European Pat. Off. . |
| 0434365 | 6/1991 | European Pat. Off. . |
| 0482797 | 4/1992 | European Pat. Off. . |
| 9301166 | 1/1993 | WIPO . |
| 9323373 | 11/1993 | WIPO . |

OTHER PUBLICATIONS

J. Am. Chem. Soc. 1991, 113, 9382–9384.
J. Med. Chem. 1992, 35, 3080–3081.
Praeklinische Forschung (2 pages) 206th Am. Chem. Soc. Nat'l. Mtg. Aug. 22–27, 1993; Chicago
Antimicrobial Agents and Chemotherapy, Nov. 1991 p. 2209–2214.
Structure and Function of the Aspartic Proteinases and pp. 395–405.

*Primary Examiner*—Shean C. Wu
*Attorney, Agent, or Firm*—Robert S. Honor; Melvyn M. Kassenoff; Thomas O. McGovern

[57] ABSTRACT

The invention relates to compounds of formula I $$R_1-A-NH-\underset{4}{CH}-\underset{\underset{OH}{|}}{CH}-\underset{2}{CH}-CO-B-NH-R_4$$

with substituents $CH_2-R_2$ on position 3 CH and $\phantom{}-R_3$ phenyl, NH on position 3 CH.

wherein the substituents have various significances.

They can be prepared by conventional methods, e.g. coupling, substitution, deprotection or protection reactions.

They possess interesting pharmacological properties and are thus indicated for use in the treatment of retroviral infections, particularly as HIV proteinase inhibitors.

5 Claims, No Drawings

2,4-DIAMINO-3-HYDROXYCARBOXYLIC ACID DERIVATIVES

The invention relates to 4-amino-3-hydroxycarboxylic acid derivatives. It concerns the compounds of formula I

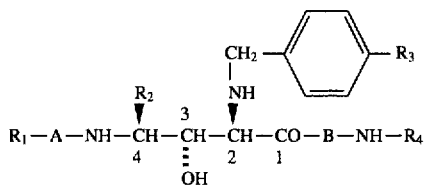

wherein

A and B independently represent a bond or an optionally substituted amino acyl moiety;

$R_1$ represents hydrogen; an amino protecting group; or a group of formula $R_5Y-$ wherein
  $R_5$ represents hydrogen or an optionally substituted alkyl, alkenyl, alkinyl, aryl, arylalkyl, heteroaryl, heteroarylalkyl, heterocyclyl or heterocyclylalkyl group; and
  Y represents —CO—; —NHCO—; —NHCS—; —SO$_2$—; —O—CO—; or —O—CS—;

$R_2$ represents the side chain of a natural amino acid; an alkyl, arylalkyl, heteroarylalkyl or cycloalkylalkyl group; or trimethylsilylmethyl, 2-thienylmethyl or styrylmethyl;

$R_3$ represents halogen, alkyl, alkoxy or hydroxyalkoxy; and $R_4$ represents 2(R)-hydroxyindan-1(S)-yl; (S)-2-hydroxy-1-phenylethyl; or 2-hydroxybenzyl optionally substituted in 4 position by methoxy; in free form or salt form;

hereinafter briefly named "the compounds of the invention".

To date, there is a definite need for finding compounds which effectively inhibit retroviruses in a human infected by such a virus, and thus treat or prevent diseases caused thereby, such as acquired immunodeficiency syndrome (AIDS).

One approach for effecting retroviral inhibition is the use of an inhibitor of a viral proteinase essential for processing viral polypeptide precursors by proteolytic maturation, e.g. the HIV proteinase.

The compounds of the present invention are antivirally active. They inhibit the HIV proteinase. They have particularly beneficial pharmacological properties, especially oral bioavailability, making them better suited for that use than structurally similar compounds.

$R_1$ preferably is hydrogen, 2-pyridylmethoxycarbonyl, benzyl-CH(OH)-carbonyl, phenoxymethylcarbonyl or an amino protecting group such as tert-butoxycarbonyl or benzyloxycarbonyl; it especially is tert-butoxycarbonyl or benzyloxycarbonyl, even more preferably benzyloxycarbonyl.

When A is an optionally substituted aminoacyl moiety, it preferably is an optionally substituted α-aminoacyl moiety such as alanine, leucine, isoleucine, asparagine, valine, tert-butylglycine, tert-leucine or histidine. It preferably is the optionally protected moiety of a natural α-amino acid, preferably of an amino acid which is a normal constitutive part of proteins, or tert-leucine. A especially is L-valine, L-tert-leucine or a bond, even more preferably L-tert-leucine.

$R_2$ preferably is the side chain of a natural amino acid, preferably of an α-amino acid, preferably of an amino acid which is a normal constitutive part of proteins. It is e.g. isopropyl, aminocarbonylmethyl, methyl, 1-methylpropyl, benzyl, 4-hydroxybenzyl or isobutyl, preferably benzyl.

When B is an optionally substituted aminoacyl moiety, it preferably is an optionally substituted α-aminoacyl moiety, such as phenylalanine, valine, leucine, isoleucine, alanine or asparagine. It preferably is the optionally substituted moiety of a natural α-amino acid, preferably of an amino acid which is a normal constitutive part of proteins. B especially is L-valine or a bond, even more preferably a bond.

$R_3$ preferably is halogen, methyl or methoxy, especially methoxy.

$R_4$ preferably is 2(R)-hydroxyindan-1(S)-yl or 2-hydroxybenzyl optionally substituted as defined above, especially 2(R)-hydroxyindan-1(S)-yl.

Y preferably is —CO— or —O—CO—, especially —O—CO—.

$R_5$ preferably is an optionally substituted alkyl, arylalkyl or heteroarylalkyl group, especially alkyl; when it is optionally substituted heteroarylalkyl it preferably is pyridylalkyl, especially 2-pyridylmethyl; when it is optionally substituted arylalkyl it preferably is benzyl-CH(OH)—; when it is substituted alkyl it preferably is phenoxymethyl.

An optionally substituted aminoacyl moiety preferably is unsubstituted. When it is substituted it e.g. is substituted by alkyl of 1 to 4 carbon atoms, such as in O-tert-butyl-L-aspartyl, or substituted at the nitrogen atom by e.g. (2-pyridylmethyl)N(methyl)CO—, (5-methyl-1,3,4-thiadiazol-2-yl)SCH$_2$CO—, (benzthiazol-2-yl)SCH$_2$CO—, (1-methyl-1,3,4-triazol-2-yl)SCH$_2$CO— or (benzimidazol-2-ylmethyl)N(methyl)CO—. It preferably has the S configuration. It preferably is an α-aminoacyl moiety, such as valine or tert-leucine.

Optionally substituted alkyl preferably is alkyl of 1 to 5 carbon atoms, preferably of 1 to 4 carbon atoms, e.g. methyl, ethyl, isopropyl or tert-butyl; it is especially of 1 or 4 carbon atoms. The substituent is e.g. phenoxy, hydroxy or optionally protected amino.

Optionally substituted arylalkyl is e.g. phenylalkyl of altogether 7 to 10 carbon atoms, such as benzyl or 2-phenylethyl; it is optionally substituted by e.g. hydroxy, such as in benzyl-CH(OH)— or phenyl-CH(CH$_2$OH)—, or is e.g. naphthylalkyl of 1 to 4 carbon atoms in the alkylene part.

An amino protecting group preferably is benzyloxycarbonyl or tert-butoxycarbonyl.

Optionally substituted heteroarylalkyl preferably is pyridylalkyl, especially 2-pyridylmethyl.

Aryl, heteroaryl and the aryl parts of arylalkyl and heteroarylalkyl may be monoor polycyclic, such as e.g. pyridyl, naphthyl, 9-fluorenylmethoxycarbonyl (FMOC) or benzimidazolyl. The alkylene part of arylalkyl or heteroarylalkyl may be substituted by e.g. hydroxy.

A heterocyclyl group, and the heterocyclyl part of a heterocyclylalkyl group, is a saturated heterocyclic group having one or more heteroatoms selected from nitrogen, oxygen and sulfur. It preferably has 5 or 6 ring constitutent atoms, and preferably up to 3 heteroatoms.

Cycloalkylalkyl preferably is cyclohexylalkyl; it preferably is of 1 to 4 carbon atoms in the alkylene part.

Halogen is fluorine, chlorine, bromine or iodine, preferably chlorine or bromine.

Alkyl and alkoxy preferably are of 1 to 4 carbon atoms, especially of 1 or 2 carbon atoms, more especially methyl or methoxy.

Hydroxyalkoxy preferably is ω-hydroxyalkoxy of 2 to 4 carbon atoms, especially 2-hydroxyethoxy.

A salt is e.g. an acid addition salt such as a hydrochloride.

The compounds of formula I have several chiral centers and can therefore exist in a variety of stereoisomers. The invention provides all stereoisomers as well as racemic mixtures unless specified otherwise. The isomers may be resolved or separated by conventional techniques, e.g. chromatographically. As appears from formula I the configuration at the carbon atom in the 2 position is R, in the 3 and 4 positions it is S.

A preferred subgroup of compounds of the invention is the compounds of formula I as defined above wherein $R_4$ is 2(R)-hydroxyindan-1(S)-yl, in free form or salt form; in another subgroup $R_4$ is (S)-2-hydroxy-1-phenylethyl; in another subgroup $R_4$ is 2-hydroxybenzyl or, preferably, 2-hydroxy-4-methoxybenzyl.

A further subgroup of compounds of the invention is the compounds of formula $Ip_1$

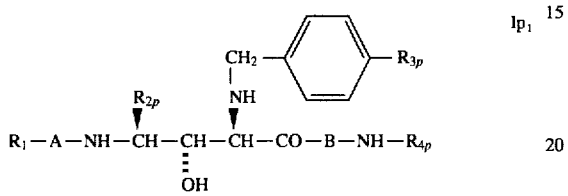

wherein $R_{2p}$ has the significance indicated above for $R_2$ with the proviso that cycloalkylalkyl represents cyclohexylalkyl, $R_{3p}$ represents alkoxy or hydroxyalkoxy, $R_{4p}$ represents 2(R)-hydroxyindan-1(S)-yl or (S)-2-hydroxy-1-phenylethyl; and the remaining substituents are as defined above, in free form or salt form.

A further subgroup of compounds of the invention is the compounds of formula $Ip_2$

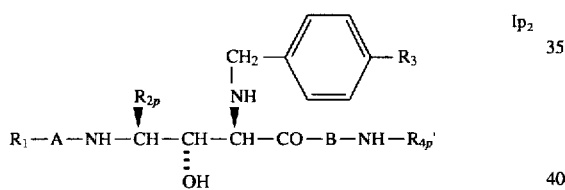

wherein $R'_{4p}$ represents 2(R)-hydroxyindan-1(S)-yl; (S)-2-hydroxy-1-phenylethyl; or 2-hydroxy-4-methoxybenzyl; and
the remaining substituents are as defined above, in free form or salt form.

A further subgroup of compounds of the invention is the compounds of formula Is

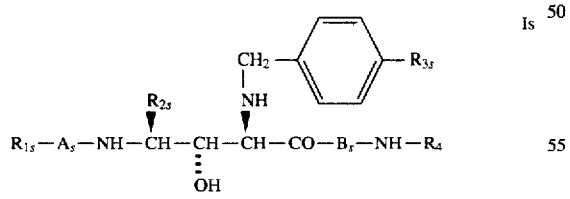

wherein $A_s$ represents a bond; L-tert-leucinoyl optionally substituted at the nitrogen atom by (5-methyl-1,3,4-thiadiazol-2-yl)—$SCH_2CO$—), (benzthiazol-2-yl)$SCH_2CO$— or (1-methyl-1,3,4-triazol-2-yl)$SCH_2CO$—; L-valinoyl optionally substituted at the nitrogen atom by (2-pyridylmethyl)N(methyl)—CO—or (benzimidazol-2-ylmethyl)N(methyl)—CO—; L-isoleucinoyl; L-aspartyl optionally substituted at the free carboxyl moiety by alkyl of 1 to 4 carbon atoms; L-asparaginoyl; or a cis-1-aminocyclopent-2-ylcarbonyl or cis-1-aminocyclohex-2-ylcarbonyl moiety optionally substituted at the nitrogen atom by (5-methyl-1,3,4-thiadiazol-2-yl)$SCH_2CO$—;

$B_s$ represents a bond or L-valinoyl;

$R_{1s}$ represents hydrogen; tert-butoxycarbonyl or benzyloxycarbonyl; or a group of formula $R_{5s}Y_s$- wherein
$R_{5s}$ represents isobutyl, 2-hydroxy-4-methoxyphenyl, imidazo[1,2-a]pyrimidin-2-yl, imidazo[1,2-a]tetrahydropyrimidin-2-yl, imidazo[1,2-a]pyrimidin-2-ylmethyl, or 2-(benzimidazol-2-yl)ethyl;

$Y_s$ represents —CO—; —NHCO—; or —O—CO—;

$R_{2s}$ represents benzyl;

$R_{3s}$ represents chlorine, bromine, methyl, methoxy, ethoxy or 2-hydroxyethoxy; and $R_4$ is as defined above,
in free form or salt form.

The compounds of the invention may be prepared by a process which comprises a) reacting a compound of formula

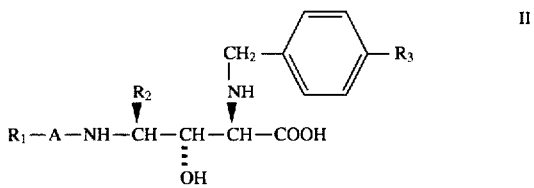

wherein the substituents are as defined above, with a compound of formula H-B-NH-$R_4$ wherein B and $R_4$ are as defined above, or b) for the preparation of the compounds of formula I wherein $R_1$ is other than hydrogen or HY-, appropriately substituting a corresponding compound of formula I wherein $R_1$ is hydrogen or HY-, and where indicated deprotecting a resultant compound of formula I in protected form, or appropriately protecting a resultant compound of formula I in unprotected form, and recovering the resultant compounds of formula I in free form or salt form.

The process variants of the invention can be effected in conventional manner for coupling amino acids. For process variant a), the compound of formula H-B-NH-$R_4$ can be in optionally protected and/or substituted form, or ester or amide forms of the reagents can be used. For process variant b), the reaction is appropriately effected with a corresponding N-terminally protected and/or substituted amino acid, or with a compound of formula $R_1$-A-Z wherein Z represents a leaving group such as a nitrophenol or N-hydroxysuccinimide and $R_1$ is as defined above.

The process variants of the invention may be effected for example in a solvent inert under the reaction conditions, such as an amide, e.g. dimethylformamide, or an ether, e.g. tetrahydrofuran, at reaction temperatures of between about room temperature (which is preferred) and the boiling point of the reaction mixture.

End products can be isolated and purified according to known methods, e.g. chromatographically.

The starting compounds can be prepared in conventional manner. The compounds of formula II can be prepared e.g. by opening the epoxy ring of compounds of formula IIc

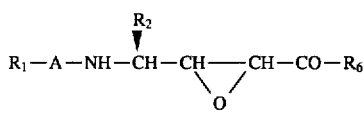

wherein $R_6$ represents optionally protected hydroxy or a group -B-NH-$R_4$ and the remaining substituents are as defined above, in the presence of an appropriate benzyl amine. This may be carried out in conventional manner, e.g. in a solvent inert under the reaction conditions, such as an ether, e.g. tetrahydrofuran, or in an alcohol, e.g. ethanol, at reaction temperatures of between about −50° C. and the boiling temperature of the reaction mixture, preferably between about −20° C. and about 80° C.

The starting compounds of formula IIc can be prepared e.g. according to the following reaction scheme:

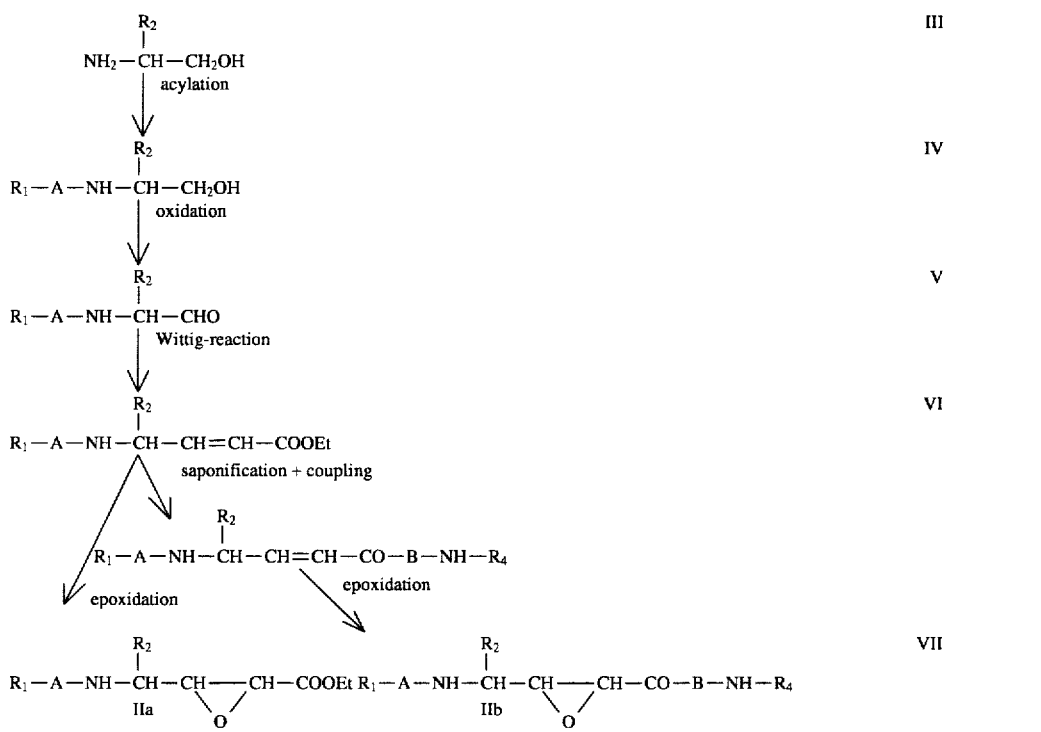

In this reaction scheme the substituents are as defined above. The single reaction steps of this reaction scheme may be carried out according to reaction conditions conventionally employed in such reactions, whereby the various intermediates can, where appropriate, be reacted further without isolation.

The remaining starting materials and intermediate compounds are either known or can be prepared according to known methods or analogously to known methods or analogously as described in the examples. 1(S)-amino-2(R)-hydroxyindan can be prepared e.g. as described in the literature (J, Am Chem. Soc. 73 [1951] 1639; J. Med. Chem. 35 [1992]1685) or via fractional crystallization of diastereoisomeric salts of racemic trans-1-amino-2-hydroxyindan, e.g. the (+)-0,0'-dibenzoyltartaric acid salts.

The following Examples illustrate the invention but are not limitative. All temperatures are in degrees centigrade. The abbreviations for amino acids follow the international (IUPAC) rules. The following further abbreviations are used:

b=in free base form
BOC=tert-butoxycarbonyl
Bz=benzyl
ch=in hydrochloride salt form
dch=in dihydrochloride salt form
depr.=deprotection
Et=ethyl
Ex.=Example
iBu=2-methylpropyl
Me=methyl
m.p.=melting point
OMe=methoxy
Phe=phenyl
prot.=protection
tLeu=tert-leucinoyl=—NHCH[—C(CH$_3$)$_3$]CO—
Z=benzyloxycarbonyl

EXAMPLE 1

4(S)-tert-Butoxycarbonylamino-3(S)-hydroxy-2(R)-(4-methoxybenzylamino)-5phenyl-pentanoic acid 1(S)-amino-2(R)-hydroxyindan-amide (process variant a)

[A,B=bond; $R_1$=BOC; $R_2$=Bz; $R_3$=OMe; $R_4$=2(R)-hydroxyindan-1(S)-yl]

390 mg of 4(S)-tert-butoxycarbonylamino-3(S)-hydroxy-2(R)-(4-methoxybenzyl-amino)-5-phenyl-pentanoic acid (compound of formula II) are dissolved in 50 ml of dimethylformamide. 130 mg of 1(S)-amino-2(R)-hydroxyindan, 120 mg of hydroxybenzotriazole and 170 mg of N-ethyl-N'-(3-dimethylaminopropyl)-carbodiimide hydrochloride are added and the mixture is stirred for 3 days at room temperature. The solvent is evaporated, ethyl acetate is added, the solution is washed with 1N HCl, saturated NaHCO$_3$ solution and brine, dried, and the solvent is evaporated. The title compound is obtained (m.p. 183°–185° - from cyclohexane/ethyl acetate 1/2).

The starting material may be prepared in the following manner:

a) 4(S)-tert-Butoxycarbonylamino-5-phenyl-pent-2(E)-enoic acid ethylester (formula VI)

3.12 ml of oxalylchloride are dissolved in 40 ml of dry dichloromethane and cooled to −55°. Then 2.81 ml of dimethylsulfoxide are added dropwise carefully and thereafter 6.98 g of BOC-L-phenylalaninol dissolved in 40 ml of dichloromethane and 3.125 ml of dimethylsulfoxide are added at −50°. The reaction mixture is stirred at −60° for one hour, reacted with triethylamine and stirred until it reaches room temperature. After dilution with 200 ml of dichloromethane the mixture is washed with 1N HCl, dried and the solvent evaporated. The residue is dissolved in toluene, 6.32 g of ethoxycarbonylmethylenetriphenylphosphorane are added and the reaction mixture is heated to 80° for 1 hour. After evaporation of the solvent, the residue is chromatographed on silicagel (solvent: toluene/ethyl acetate 4/1) (m.p. 47°).

b) 4(S)-tert-Butoxycarbonylamino-2(S),3(R)-epoxy-5-phenyl-pentanoic acid ethylester (formula IIc)

3 g of 4(S)-tert-Butoxycarbonylamino-5-phenyl-pent-2(E)-enoic acid ethylester are dissolved in 30 ml of dichloromethane. 1.37 g of m-chloroperbenzoic acid are added and the reaction mixture is stirred for 5 days. After evaporation of the solvent, the residue is chromatographed on silicagel (solvent: toluene/ethyl acetate 4/1) (m.p. 55°–61°).

c) 4(S)-tert-Butoxycarbonylamino-3(S)-hydroxy-2(R)-(4-methoxybenzylamino)-5-phenyl-pentanoic acid ethylester 12.8 g of 4(S)-tert-butoxycarbonyl-2(S),3(R)-epoxy-5-phenyl-pentanoic acid ethylester are dissolved in 100 ml of ethanol. 10 g of 4-methoxybenzylamine are added and the solution is stirred at 70° for 12 hours. The solvent is evaporated and the residue is chromatographed on silicagel (solvent: cyclohexane/ethyl acetate 3/1) (oil).

d) 4(S) -tert-Butoxycarbonylamino-3(S)-hydroxy-2(R)-(4-methoxybenzylamino)-5-phenyl-pentanoic acid (formula II)

9 g of 4(S)-tert-butoxycarbonylamino-3(S)-hydroxy-2(R)-(4-methoxybenzylamino)-5-phenyl-pentanoic acid ethylester are dissolved in 300 ml of tetrahydrofuran and 22 ml of 1 N aqueous sodium hydroxide solution are added. The reaction mixture is stirred for 16 hours at room temperature and diluted with 300 ml of water. Tetrahydrofuran is evaporated and the aqueous solution is washed with ethyl acetate. Acidification with 1N HCl leads to a white precipitate which is filtered off and dried (m.p.: 203°–206°).

EXAMPLE 2

4(S)-(Benzyloxycarbonyl-L-tert-leucinoy)amino-3(S)-hydroxy-2(R)-(4-methoxybenzylamino)-5-phenyl-pentanoic acid 1(S)-amino-2(R)-hydroxyindan-amide (process variant b)

[A=L-tLeu; B=bond; $R_1$=Z; $R_2$=Bz; $R_3$=OMe; $R_4$=2(R)-hydroxyindan1(S)-yl]

360 mg of N-methylmorpholine are added to a solution of 850 mg of 4(S)-amino-3(S)-hydroxy-2(R)-(4-methoxybenzylamino)-5-phenyl-pentanoic acid 1(S)-amino-2(R)-hydroxyindan-amide dihydrochloride (compound of Example 3) in 20 ml of dimethylformamide. 480 mg of N-benzyloxycarbonyl-L-tert-leucine, 290 mg of 3,4-dihydro-3-hydroxy-4-oxo-1,2,3-benzotriazine and 340 mg of N-ethyl-N'-(3-dimethylaminopropyl)-carbodiimide hydrochloride are added and the solution is stirred for 3 days at room temperature. The solvent is evaporated, ethyl acetate is added, the mixture is washed with 1N HCl, saturated $NaHCO_3$ solution and brine. The organic layer is dried, the solvent is evaporated and the residue is chromatographed on silicagel (solvent: cyclohexane/ethyl acetate 1/2). The title compound is obtained [m.p.: 146°–148° - from ether; $[\alpha]^{20}_D$=−28.9° (c=1, $CH_3OH$); m.p. of hydrochloride: 128°–134°-from ether; $[\alpha]^{20}_D$=−16.8° (C=1, $CH_3OH$)].

EXAMPLE 3

4(S)-Amino-3(S)-hydroxy-2(R)-(4-methoxybenzylamino)-5-phenyl-pentanoic acid 1(S)-amino-2(R)-hydroxyindan-amide (deprotection)

[A,B=bond; $R_1$=H; $R_2$=Bz; $R_3$=OMe; $R_4$=2(R)-hydroxyindan-1(S)-yl]

6 g of 4(S)-tert-butoxycarbonylamino-3(S)-hydroxy-2(R)-(4-methoxybenzyl-amino)-5-phenyl-pentanoic acid 1(S)-amino-2(R)-hydroxyindan-amide (compound of Example 1) are dissolved in a mixture of 20 ml of dichloromethane and 4 ml of methanol. 300 ml of a 3 N solution of HCl in diethylether are added and the mixture is stirred for 3 hours at room temperature. The white precipitate is filtered off, washed with diethylether and dried in vacuo. The title compound is obtained in dihydrochloride salt form (m.p.: 147°–151°).

Example 4

N-{4(S)-[(N-Benzyloxycarbonyl-tert-leucinoyl)amino]-3-(S)-hydrox-2(R)-(4-methoxybenzylamino)-5-phenyl}pentanoyl-L-valine-N-[(2-hydroxy-4-methoxy)benzyl]amide (protection)

[A=L-tLeu; B=L-Val; $R_2$=Z; $R_2$=Bz; $R_3$=OMe; $R_4$=2-OH, 4-OMe-Bz]

182 mg of 4(S)-[(N-(L-tert-leucinoyl)amino]-3(S)-hydroxy-2(R)-(4-methoxy-benzylamino)-5-phenyl]pentanoyl-L-valine-N-[(2-hydroxy-4-methoxy)benzyl]amide (compound of Example 30) are dissolved in 20 ml of dimethylformamide. 34 µl of triethylamine and 62.3 mg of N-(benzyloxycarbonyloxy)-succinimide are added and the mixture is stirred at room temperature for 3 days. The solvent is evaporated and the residue is chromatographed on silicagel (solvent: ethyl acetate/methanol 98/2). The title compound is obtained (m.p.: 82°–89°).

| Ex. No. | $R_1$ | A | $R_3$ | B | $R_4$ | Process variant | m.p. |
|---|---|---|---|---|---|---|---|
| A) $R_2$ = Bz: | | | | | | | |
| 5 | BOC | bond | OMe | bond | (S)—CH(Phe)$CH_2$OH | a) | b 65–68° |
| 6 | BOC | bond | O($CH_2$)$_2$OH | bond | 2(R)-hydroxyindan-1(S)-yl | a) | b 77–82° |
| 7 | BOC | bond | OEt | bond | 2(R)-hydroxyindan-1(S)-yl | a) | b 65–69° |
| 8 | BOC | bond | Br | bond | 2(R)-hydroxyindan-1(S)-yl | a) | b 186–189° |

-continued

| Ex. No. | R₁ | A | | R₃ | Process variant | m.p. |
|---|---|---|---|---|---|---|
| 9 | BOC | bond | Cl | bond | 2(R)-hydroxyindan-1(S)-yl | a) | b 180–183° |
| 10 | BOC | L-tLeu | OMe | bond | 2(R)-hydroxyindan-1(S)-yl | a) | b 180–195° |
| 11 | BOC | L-tLeu | OMe | L-Val | 2-OH,4-OMe—Bz | a) | b 85–92° |
| 12 | BOC | L-tLeu | OMe | L-Val | 2-OH—Bz | a) | b 83–92° |
| 13 | Z | L-tLeu | OMe | bond | (S)—CH(Phe)CH₂OH | b) | b 143–147° |
| 14 | Z | L-tLeu | O(CH₂)₂OH | bond | 2(R)-hydroxyindan-1(S)-yl | b) | b 109–113° |
| 15 | Z | L-tLeu | OEt | bond | 2(R)-hydroxyindan-1(S)-yl | b) | b 104–109° |
| 16 | Z | L-tLeu | Cl | bond | 2(R)-hydroxyindan-1(S)-yl | b) | b 134–136° |
| 17 | Z | L-tLeu | Br | bond | 2(R)-hydroxyindan-1(S)-yl | b) | b 148–151° |
| 18 | Z | L-Val | OMe | bond | 2(R)-hydroxyindan-1(S)-yl | b) | b 81–91° |
| 19 | H | L-Val[1] | OMe | bond | 2(R)-hydroxyindan-1(S)-yl | b) | b 70–76° |
| 20 | H | L-tLeu[2] | OMe | bond | 2(R)-hydroxyindan-1(S)-yl | b) | b 88–95° |
| 21 | H | L-tLeu[2] | OMe | L-Val | 2-OH,4-OMe—Bz | b) | b 95–98° |
| 22 | Z | L-Val | OMe | L-Val | 2-OH,4-OMe—Bz | b) | b 78–82° |
| 23 | H | bond | OMe | bond | (S)—CH(Phe)CH₂OH | depr. | dch 134–136° |
| 24 | H | bond | O(CH₂)₂OH | bond | 2(R)-hydroxyindan-1(S)-yl | depr. | |
| 25 | H | bond | OEt | bond | 2(R)-hydroxyindan-1(S)-yl | depr. | |
| 26 | H | bond | OMe | bond | 2(R)-hydroxyindan-1(S)-yl | b) | dch 185–190° |
| 27 | H | bond | Br | bond | 2(R)-hydroxyindan-1(S)-yl | depr. | dch 151–156° |
| 28 | H | bond | Cl | bond | 2(R)-hydroxyindan-1(S)-yl | depr. | dch 160–164° |
| 29 | H | L-tLeu | OMe | bond | 2(R)-hydroxyindan-1(S)-yl | depr. | dch 185–190° |
| 30 | H | L-tLeu | OMe | L-Val | 2-OH,4-OMe—Bz | depr. | dch 178–181° |
| 31 | H | L-tLeu | OMe | L-Val | 2-OH—Bz | depr. | dch R_f = 0.1[8] |
| 32 | Z | L-tLeu | OMe | L-Val | 2-OH—Bz | prot. | b 73–80° |

B) $R_2 = Bz$; $B =$ a bond; $R_4 = 2(R)$-hydroxyindan-1(S)-yl:

| Ex. No. | R₁ | A | R₃ | Process variant | m.p. |
|---|---|---|---|---|---|
| 33 | imidazo[1,2-a]pyrimidin-2-yl-CO— | L-tLeu | OMe | b) | b 104–110° |
| 34 | (2,4-di-OMe—Phe)—NHCO— | L-tLeu | OMe | b) | b 102–105° |
| 35 | 2-(benzimidazol-2-yl)ethyl-CO— | L-tLeu | OMe | b) | b 130–134° |
| 36 | iBu—OCO— | bond | OMe | b) | b 123–125° |
| 37 | imidazo[1,2-a]tetrahydropyrimidin-2-yl-CO— | L-tLeu | OMe | b) | b 118–125° |
| 38 | imidazo[1,2-a]pyrimidin-2-ylmethyl-CO— | L-tLeu | OMe | b) | b 110–120° |
| 39 | H | L-tLeu[3] | OMe | b) | b 90–95° |
| 40 | H | L-tLeu[4] | OMe | b) | b 95–108° |
| 41 | Z | L-Val | OEt | b) | b 138–140° |
| 42 | Z | L-Val | O(CH₂)₂OH | b) | b 86–87° |
| 43 | Z | L-iLeu | OMe | b) | b 112–115° |
| 44 | Z | L-(O-tBu)Asp | OMe | b) | b 70–75° |
| 45 | Z | L-Asp | OMe | b);depr. | ch 111–114° |
| 46 | Z | L-Asn | OMe | b) | b 158–162° |
| 47[5] | BOC | cis-1-aminocyclopent-2-ylCO— | OMe | b) | b 79–82° |
| 48[6] | BOC | cis-1-aminocyclopent-2-ylCO— | OMe | b) | b 70–78° |
| 49[5] | BOC | cis-1-aminocyclohex-2-ylCO— | OMe | b) | b 78–86° |
| 50[6] | BOC | cis-1-aminocyclohex-2-ylCO— | OMe | b) | b 82–93° |
| 51[5] | H | cis-1-aminocyclohex-2-ylCO— | OMe | depr. | dch 103–107° |
| 52[6] | H | cis-1-aminocyclohex-2-ylCO— | OMe | depr. | dch 128–138° |
| 53[5] | H | cis-1-aminocyclopent-2-ylCO— | OMe | depr. | dch 98–102° |
| 54[6] | H | cis-1-aminocyclopent-2-ylCO— | OMe | depr. | dch 115-120° |
| 55[5] | H | cis-1-aminocyclopent-2-ylCO—[2] | OMe | b) | b 75–83° |
| 56[6] | H | cis-1-aminocyclopent-2-ylCO—[2] | OMe | b) | b 83–90° |
| 57 | (2-OH,4-OMe—Phe)—NHCO— | L-Val | OMe | b) | b 95–105° |
| 58 | BOC | bond | Me | a) | b 71–73° |
| 59 | H | bond | Me | depr. | dch 145–151° |
| 60 | Z | L-tLeu | Me | b) | b 88–93° |
| 61 | H | L-Val[7] | OMe | b) | b 106–109° |

[1]Substituted at N atom with (2-pyridylmethyl)N(CH₃)CO—
[2]Substituted at N atom with (2-methyl)-1,3,4-thiadiazol-2-yl)SCH₂CO—
[3]Substituted at N atom with (benzthiazol-2-yl)SCH₂CO—
[4]Substituted at N atom with (1-methyl-1,3,4-triazol-2-yl)SCH₂CO—
[5]Isomer A with respect to configuration at cycloalkyl ring
[6]Isomer B with respect to configuration at cycloalkyl ring
[7]Substituted at N atom with (benzimidazol-2-ylmethyl)N(CH₃)CO—
[8]In toluene/ethyl acetate ½

FURTHER INTERMEDIATES:

A) Compounds of formula II

Analogously as described above under Example 1 the following compounds of formula II are obtained wherein $R_2=Bz$ and $R_1$, A and $R_3$ respectively are:

BOC, a bond and 2-hydroxyethoxy (m.p. 218°–221°);

BOC, a bond and ethoxy (m.p. 191°–194°);

BOC, L-tLeu and OMe (m.p. 124°–125°);

BOC, a bond and Br (m.p. 214°–217°);

BOC, a bond and Cl (m.p. 111°–115°).

B) BOC-L-tert-leucinoyl-L-phenylalaninol 25 g of tert-butyloxycarbonyl-L-tert-leucine are dissolved in 250 ml of dry dimethylformamide, 16.36 g of phenylalaninol, 14.62 g of hydroxybenzotriazole and 24.9 g of N-ethyl-N'-(3-dimethylaminopropyl)carbodiimide hydrochloride are added. The mixture is stirred for one day. The precipitate is filtered off, washed carefully with ethyl acetate and dried in vacuo (m.p. 198°–201°).

C) L-Valine-[(2-hydroxy-4-methoxy)benzyl]amide a) 2-Hydroxy-4-methoxy-benzaldehydoxime 10 g of 2-hydroxy-4-methoxy-benzaldehyde are dissolved in 200 ml of ethanol. 6.9 g of hydroxylamine hydrochloride and 13.7 ml of triethylamine are added and the mixture is stirred for 5 hours at room temperature. The solvent is evaporated, the residue is taken up in ethyl acetate and the organic layer is washed with $NaHCO_3$-solution and water. After drying over $MgSO_4$, the solvent is evaporated and the residue is used for the next step without further purification.

b) 2-Hydroxy-4methoxy-benzylamine 11.1 g of 2-hydroxy-4-methoxy-benzaldehydoxime are dissolved in 400 ml of methanol containing 40 ml of formic acid. 1 g of palladium on charcoal is added and the solution is hydrogenated for 3 hours at room temperature. After filtration, the solvent is evaporated and the residue is chromatographed on silicagel (solvent: ethyl acetate/methanol 5/1+2% $NH_3$-solution) to give an oil:

$^1$H-NMR (DMSO): 3.67 (s,3H); 3.78 (bs,2H); 4.70 (bs,1H, exchangeable); 6.25 (d, J=9Hz, 1H); 6.30 (s, 1H); 6.95 (d, J=9Hz, 1H).

c) N-tert-Butyloxycarbonyl-L-valine-[(2-hydroxy-4-methoxy)benzyl]amide 306 mg of 2-hydroxy-4-methoxy-benzylamine are added to a solution of 676 mg of tert-butyloxycarbonyl-L-valine-p-nitrophenylester in 10 ml of dimethylformamide under argon. The reaction mixture is stirred for 2 days at room temperature. After evaporation of the solvent, the residue is dissolved in ethyl acetate and washed with 0.1 N NaOH, water and brine. The organic phase is dried over $MgSO_4$, the solvent is removed and the residue is chromatographed on silicagel (solvent: toluene/ethyl acetate 2/1). The product is obtained as a solid (m.p. 41°–45°).

d) L-Valine-[(2-hydroxy-4-methoxy)benzyl]amide

A solution of 400 mg of N-tert-butyloxycarbonyl-L-valine-[(2-hydroxy-4methoxy)benzyl]amide and 1.5 ml of trifluoroacetic acid in 10 ml of dichloromethane is stirred for 5 hours at room temperature. The dichloromethane is removed, the residue is taken up in ethyl acetate and washed several times with 5% $NaHCO_3$-solution and then brine. The organic phase is dried over $MgSO_4$, the solvent is evaporated yielding the product as an oil:

$^1$H-NMR (CDCl$_3$): 0.80 (d, J=10Hz, 3H); 1.00 (d, J=10Hz, 3H); 2.25–2.40 (m, 1H); 3.23 (d, J=3.6Hz, 1H); 3.76 (s, 3H); 4.20–4.40 (m, 2H); 6.37 (dd, J=2.6Hz, J=8.3Hz, 1H); 6.50 (d, J=2.6Hz, 1H); 6.98 (d, J=8.3Hz, 1H); 8.24 (bs, 1H).

D) L-Valine-[(2-hydroxy)benzyl]amide Is obtained as an oil analogously as described above under C):

$^1$H-NMR: d=0.79 (d, 3H); 1.00 (d, 3H); 2.37 (dsep, 1H); 3.30 (d, 1H); 4.20–4.41 (m, 2H); 6.81 (t, 1H); 6.93 (d, 1H); 7.08 (d, 1 H); 7.20 (t, 1H); 8.22 (bs, 1H).

The compounds of formula I in free form or in pharmaceutically acceptable salt, e.g. acid addition salt form, hereinafter briefly named "the agents of the invention", possess interesting pharmaceutical properties. They are therefore useful as pharmaceuticals. In particular, they exhibit antiviral activity, especially HIV-proteinase inhibiting activity, whereby they possess only low or inexistent inhibiting activity against human proteinases such as renin or pepsin. Further, they have particularly pronounced oral bioavailability over conventional peptidic anti-HIV proteinase agents. This activity can be shown in the following tests:

1. Assay of peptide cleavage by HIV-proteinase

Inhibition of HIV-proteinase is measured as described in the literature: A. Richards et al., *J. Biol. Chem.* 265, 773–7736 (1990) and L. H. Philip et al., *Biochem. Biophys. Res. Comun.* 171,439–444 (1990). Briefly the peptide H-Lys-Ala-Arg-Val-Leu-Nph-Glu- Ala-Nle-$NH_2$ (where Nph is p-nitrophenylalanine and Nle is norleucine) is used as substrate for recombinant HIV-1- and HIV-2-proteinase. Cleavage occurs between the Leu and Nph residues. The reaction is followed spectrophotometrically by the decrease in extinction at 300 nm which is observed upon cleavage.

In this test the agents of the invention exhibit $K_i$-values of from about 3 nM to about 1 μM for HIV-1-proteinase and of from about 8 nM to about 10 μM for HIV-2-proteinase.

2. Cellular assay

Inhibition of the HIV-1 (HTLV III$_B$)-induced cytopathic effect is measured in MT4-cells as described in the literature (R. Pauwels et al, *J. Virol. Meth.* 20 309–321 [1988]). Briefly, an HTLV-1 transformed T4 cell line, MT$_4$, which has been shown previously to be highly permissive to HIV infection, serves as a target cell line. Inhibition of HIV-induced cytopathic effect is used as the end point. The viability of both HIV- and mock-infected cells is assessed spectrophotometrically via the in situ-reduction of 3-(4,5-dimethylthiazol-2-yl)-2,5-diphenyltetrazolium bromide (MTT). The comparison of the effects of various concentrations of the agent on HIV- versus mock-infected cells allows the determination of cytotoxic ($TC_{50}$) and virus-inhibitory ($IC_{50}$) concentrations.

In this test the agents of the invention exhibit $IC_{50}$-values of from about 10 nM to about 1 μM. 3. Assay of oral bioavailability in mice As is known from the literature, peptide based drugs characteristically show poor oral bioavailability. Since with HIV patients long term medication with proteinase inhibitors is anticipated, it is important that a useful drug be orally bioavailable. This is one of the main obstacles in the development of effective drugs in this peptidic structural class. Surprisingly, the agents of the invention show excellent bioavailabilty after oral administration. This can be shown e.g. in the following test:

For peroral administration, a solution of the test substance (25 mg/ml) in a suitable solvent such as Cremophor RH40$^R$/ Maisine$^R$ /propylene glycol / ethanol (38/32/15/15) is prepared. Female Balb/c mice are fasted for 24 hours prior to the start, and throughout the experiment water is given ad libitum. At various times following drug administration, blood samples are obtained by sacrificing animals under anaesthesia by cutting the vena jugularis, followed by cervical dislocation. Samples are collected in heparinized tubes (typically 0.4–0.6 ml). For sample analysis solid phase extraction and HPLC are used. Drug concentration in the samples is calculated by least-squares linear regression analysis of the peak area ratio (inhibitor/internal standard) of spiked blood standards versus concentration. From the concentration versus time data, the "Area Under the Curve" (AUC) value is calculated by the trapezoidal rule.

In this test the agents of the invention exhibit AUC-values of from about 25 μM.h to about 160 μM.h. at a dose of 125 mg/kg.

The agents of the invention are therefore useful as pharmaceuticals, particularly as anti-HIV-proteinase agents, e.g. in the prophylaxy and treatment of retroviral infections. For this use, the effective dosage will, of course, vary depending on the particular agent employed, the mode of administration and the treatment desired. However, in general, satisfactory results are obtained when the agents are administered at a daily dosage of from about 0.02 mg/kg to about 50 mg/kg animal body weight, suitably given in divided doses two to four times daily. For most large mammals the total daily dosage is from about 1 mg to about 3500 mg, preferably from about 10 mg to about 2000 mg, especially from about 500 mg to about 1500 mg, especially about 600 mg given once or twice daily.

The agents may be administered in similar manner to known standards for use in such indications. It appears likely that metabolisation occurs according to known patterns for structurally related compounds, e.g., for the agents of the invention wherein $R_4$ is 2(R)-hydroxyindan-1(S)-yl, starting with hydroxylation at the 3 or 4 position of the indanyl moiety.

The agent of Example 2, i.e. 4(S)-(benzyloxyrcarbonyl-L-tert-leucinoyl)amino-3(S)-hydroxy-2(R)-(4-methoxybenzylamino)-5-phenyl-pentanoic acid 1(S)-amino2(R)-hydroxy-indan-amide in free form or in pharmaceutically acceptable salt form is the preferred agent of the invention as an anti-HIV-proteinase agent. It inhibits HIV-1 proteinase with $K_i$=9.5 nM and HIV-2 proteinase with $K_i$=50 nM, and further has excellent oral uptake. It is specific for the retroviral enzymes since it does not inhibit endogenous proteinases such as renin and cathepsin D. In the cellular assay it has an $IC_{50}$ of 0.25 μM. It is indicated that for this anti-HIV indication this agent may be administered to larger mammals, for example humans, by similar modes of administration at similar or lower dosages than conventionally employed with known standards for such indications.

The invention also concerns a method of treating retroviral diseases, especially diseases caused by HIV, which comprises administering to a subject in need of such treatment an effective amount of an agent of the invention, as well as the agents of the invention for use as pharmaceuticals, particularly in the treatment of retroviral diseases, especially of diseases caused by HIV, especially as agents against HIV-proteinase.

The agents may be admixed with conventional chemotherapeutically acceptable diluents and carriers and administered e.g. parenterally or intravenously, preferably orally, in such forms as tablets or capsules. The concentrations of active substance will, of course, vary depending e.g. on the agent employed, the treatment desired and the nature of the form.

Such compositions form part of the invention. The invention thus also includes pharmaceutical compositions comprising an agent of the invention together with at least one pharmaceutically acceptable carrier or diluent.

Stable compositions for oral administration that offer high absorption efficiency and drug loading can be obtained by formulating an agent of the invention with a carrier medium comprising a hydrophilic phase, a lipophilic phase and a surfactant. Preferably the composition is in the form of a "microemulsion preconcentrate" or "emulsion preconcentrate", in particular of the type providing o/w (oil-in-water) microemulsions or emulsions. However the composition may be in the form of a microemulsion or an emulsion which additionally contains an aqueous phase, preferably water. A "microemulsion preconcentrate" is a formulation which spontaneously forms a microemulsion in an aqueous medium, for example in water or in the gastric juices after oral application. A "microemulsion" is a non-opaque or substantially non-opaque colloidal dispersion that is formed spontaneously or substantially spontaneously when its components are brought into contact. A microemulsion is thermodynamically stable. An "emulsion preconcentrate" is a formulation which spontaneously forms an emulsion in an aqueous medium, for example in water or in the gastric juices, after oral application. The emulsion formed is opaque and thermodynamically stable. The lipophilic phase may comprise about 10 to 85% by weight of the carrier medium; the surfactant may comprise about 5 to 80% by weight of the carrier medium; the hydrophilic phase may comprise about 10 to 50% by weight of the carrier medium. The agent of the invention is preferably present in an amount of about 1 to 15% by weight of the composition, more preferably about 2 to 10%.

The hydrophilic phase may be selected from e.g. Transcutol$^R$ (which has the formula $C_2H_5[O—(CH_2)_2]_2$-OH), Glycofurol$^R$ (also known as tetrahydrofurfuryl alcohol polyethylene glycol ether) and 1,2-propylene glycol, or mixtures thereof, and is preferably 1,2-propylene glycol it may include further hydrophilic co-components, for example lower alkanols such as ethanol.

Preferred lipophilic phase components are medium chain fatty acid triglycerides, mixed mono-, di-, tri-glycerides, and transesterified ethoxylated vegetable oils. Suitable medium chain fatty acid triglycerides are those known and commercially available under the trade names Miglyol$^R$, Captex$^R$, Myritol$^R$, Capmul$^R$, Captex$^R$, Neobee$^R$ and Mazol$^R$; Miglyol 812$^R$ being the most preferred. The mixed mono-, di-, triglycerides preferably comprise mixtures of $C_{12-20}$ fatty acid mono-, di- and tri-glycerides, especially mixed $C_{16-18}$ fatty acid mono-, di- and triglycerides. The fatty acid component of the mixed mono-, di- and tri-glycerides may comprise both saturated and unsaturated fatty acid residues. The transesterified ethoxylated vegetable oils comprise transesterification products of, for example, almond oil, ground nut oil, olive oil, peach oil, palm oil or, preferably, corn oil, sunflower oil or safflower oil and most preferably corn oil, with glycerol. They are generally obtained by heating the selected vegetable oil with glycerol, at high temperature in the presence of an appropriate catalyst under an inert atmosphere with continous agitation (for example in a stainless steel reactor) to effect trans-esterification or glycerolysis. In addition to their mono-, di- and tri-glyceride components, the transesterification products also generally comprise minor amounts of free glycerol. Preferably some of the glycerol is first removed to give a "substantially glycerol free batch" when soft gelatine capsules are to be made.

Trans-esterification products of corn oil and glycerol provide particularly suitable mixed mono-, di-, and tri-glycerides. An example of a suitable mixed glyceride product is the trans-esterification product commercially available under the trade name Maisine$^R$. This product is comprised predominantly of linoleic and oleic acid mono-, di- and tri-glycerides together with minor amounts of palmitic and stearic acid mono-, di- and triglycerides (corn oil itself being comprised of about 56% by weight linoleic acid, 30% oleic acid, about 10% palmitic and about 3% stearic acid constituents). The physical characteristics of Maisine$^R$ [available from Etablissements Gattefossé, of 36, Chemin de Genas, P.O. Box 603, 69804 Saint-Priest, Cedex (France)] are: up to 10% (typically 3.9 to 4.9% or, in "substantially glycerol free" batches, about 0.2%) free glycerol; about 35% (typically 30 to 40% or, in "substantially glycerol free" batches, about 32 to 36%, for example about 36%) monoglycerides; about 50% (or, in "substantially glycerol free" batches, about 46 to 48%) di-glycerides; about 10% (or, in "substantially glycerol free" batches, about 12 to 15%) tri-glycerides; and about 1% free oleic acid. The fatty acid content for Maisine$^R$ is typically: about 11% palmitic acid; about 2.5% stearic acid; about 29% oleic acid; about 56% linoleic acid; and 1.5% other acids.

If the agent of the invention is to be administered in the form of a microemulsion or emulsion, it is preferred that the mixed mono-, di-, and tri-glycerides are clear and remain clear for more than 20 days upon storage at temperatures of 20° C. to 25° C. Also, a sample of the mixed mono-, di-, and tri-glycerides, which has been kept in a refrigerator at about between 2° and 8° C. for 24 hours and then held at room temperature for 1 hour, should be clear. Also the mono-, di-, tri-glycerides preferably have a low saturated fatty acid content. Mixed mono-, di-, tri-glycerides meeting these requirements may be obtained from commercially available products by separation techniques as known in the art (for example freezing procedures coupled with separation techniques such as centrifugation) to remove the saturated fatty acid components and enhance the unsaturated fatty acid component content. Typically the total saturated fatty acid component will be less than 15% (for example <10%, or <5%) by weight based on the total weight of the lipophilic phase. A reduction of the content of saturated fatty acid component in the mono-glyceride fraction may be observed after being subjected to the separation technique. A suitable process is described in WO 93/09211.

The lipophilic phase may alternatively comprise suitable transesterified ethoxylated vegetable oils such as those obtained by reacting various natural vegetable oils with polyethylene glycols that have an average molecular weight of from 200 to 800, in the presence of an appropriate catalyst. The procedures are known and an example is described in U.S. Pat. No. 3 288 824. Transesterified ethoxylated corn oil is particularly preferred. Transesterified ethoxylated vegetable oils are known and are commercially available under the trade name Labrafil$^R$. Examples are Labrafil M 2125 CS$^R$ and Labrafil M 1944 CS$^R$. Labrafil M 2130 CS$^R$ may also be used. A preferred transesterified ethoxylated vegetable oil is Labrafil M 2125 CS$^R$.

Examples of suitable surfactants are:

i) reaction products of a natural or hydrogenated castor oil and ethylene oxide. Various surfactants are commercially available. The polyethyleneglycol-hydrogenated castor oils available under the trade name Cremophor$^R$ are especially suitable. Particularly suitable are Cremophor RH 40$^R$, which has a saponification number of about 50 to 60, an acid number of less than about 1, a water content of less than about 2%, an $n_D^{60}$ of about 1.453 to 1.457 and an HLB (hydrophilic/lipophilic balance) of about 14 to 16; and Cremophor RH60$^R$, which has a saponification number of about 40 to 50, an acid number of less than about 1, an iodine number of less than about 1, a water content of about 4.5 to 5.5% an $n_d^{25}$ of about 1.453 to 1.457 and an HLB of about 15 to 17. Also suitable are polyethyleneglycol castor oils such as that available under the trade name Cremophor EL$^R$. Similar or identical products which may also be used are available under the trade names Nikkol$^R$ (e.g. Nikkol HCO-40$^R$ and HCO-60$^R$), Mapeg$^R$ (e.g. Mapeg CO-40$^R$), Incrocas$^R$ (e.g. Incrocas 40$^R$), and Tagat$^R$ (e.g. Tagat RH 40$^R$).

ii) Polyoxyethylene-sorbitan-fatty acid esters, for example mono- and tri-lauryl, palmityl, stearyl and oleyl esters of the type known and commercially available under the trade name Tween$^R$. Especially preferred products of this class are Tween 40$^R$ and Tween 80$^R$.

iii) Polyoxyethylene fatty acid esters, for example polyoxyethylene stearic acid esters of the type known and commercially available under the trade name Myrj$^R$. An especially preferred product of this class is Myrj 52$^R$.

iv) Polyoxyethylene-polyoxypropylene co-polymers and block co-polymers, for example of the type known and commercially available under the trade names Pluronic$^R$, Emkalyx$^R$ and Poloxamer$^R$. Especially preferred products of this class are Pluronic F68$^R$ and Poloxamer 188$^R$.

v) Dioctylsulfosuccinate or di-[2-ethylhexyl]-succinate.

vi) Phospholipids, in particular lecithins. Suitable lecithins include, in particular, soya bean lecithins. vii) Propylene glycol mono- and di-fatty acid esters such as propylene glycol dicaprylate (also known and commercially available under the trade name Miglyol 840$^R$), propylene glycol dilaurate, propylene glycol hydroxystearate and so forth.

The surfactant selected preferably has an HLB (hydrophilic/lipophilic balance) of at least 10.

Full physical characteristics of the products referred to herein by trade name can be obtained e.g. from H. P. Fiedler, "*Lexikon der Hilfsstoffe fir Pharmazie, Kosmetik und Angrenzende Gebiqte*", Editio Cantor, D-7960 Aulendorf, Germany, 3rd revised and expanded edition (1989). Preferably the relative proportion of hydrophilic phase component(s), the lipophilic phase and the surfactant lie within the "microemulsion" region on a standard three way plot. The compositions thus obtained are microemulsion preconcentrates of high stability.

Alternatively the components may be selected to provide an emulsion preconcentrate. The emulsion preconcentrate compositions also show good stability characteristics.

The pharmaceutical compositions may also include further additives or ingredients, for example antioxidants. They exhibit especially advantageous properties when administered orally, for example in terms of consistency and high level of bioavailability obtained in standard bioavailability trials. Pharmacokinetic parameters, for example absorption and blood levels, also become surprisingly more predictable and problems in administration with erratic absorption may be eliminate or reduced. Additionally the pharmaceutical composition is effective with tenside materials, for example bile salts, present in the gastro-intestinal tract.

The pharmaceutical compositions for oral use are preferably compounded in unit dosage form, for example by filling them into orally administrable capsule shells. The capsule shells may be soft or hard gelatine capsule shells. However, if desired the pharmaceutical compositions may be in a drink solution form and may include water or any other aqueous system, to provide emulsion or microemulsion systems suitable for drinking.

The invention further concerns a process for the preparation of a medicament, particularly of a medicament against retroviral diseases, which comprises mixing an agent of the invention together with at least one pharmaceutically acceptable carrier or diluent, and the use of such an agent in the manufacture of a medicament, particularly of a medicament against retroviral diseases.

We claim:

1. A compound of formula is in the (2R,3S,4S) configuration

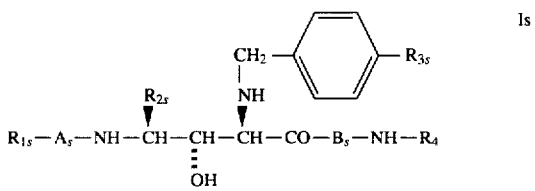

wherein

A$_S$ represents a bond; L-tert-leucinoyl optionally substituted at the nitrogen atom by (5-methyl-1,3,4-thiadiazol-2-yl) SCH$_2$CO—, (benzthiazol-2-yl)SCH$_2$CO— or (1-methyl-1,3,4-triazol-2-yl)SCH$_2$CO—; L-valinoyl optionally substituted at the nitrogen atom by (2-pyridylmethyl)-N(methyl)—CO— or (benzimidazol-2- ylmethyl)N(methyl)—CO—; L-isoleucinoyl; L-aspartyl optionally substituted at the free carboxyl moiety by alkyl of 1 to 4 carbon atoms; L-asparaginoyl; or cis-1-aminocyclopent-2-ylcarbonyl or cis-1-aminocyclohex-2-ylcarbonyl optionally substituted at the nitrogen atom by (5-methyl-1,3,4-thiadiazol-2-yl)SCH$_2$CO—;

$B_s$ represents a bond or L-valinoyl;

$R_{1s}$ represents hydrogen; tert-butoxycarbonyl, benzyloxycarbonyl; or a group of formula $R_{ss}Y_s$— wherein $R_{ss}$ represents isobutyl, 2-hydroxy-4-methoxyphenyl, imidazo[1,2-a]pyrimidin-2-yl, imidazo[1,2-a]tetrahydropyrimidin-2-yl, imidazo[1,2-a]pyrimidin-2-ylmethyl, or 2-(benzimidazol-2-yl)ethyl;

$Y_s$ represents —CO; —NHCO; or —O—CO;

$R_{2s}$ represents benzyl;

$R_{3s}$ represents chlorine, bromine, methyl, methoxy, ethoxy or 2-hydroxyethoxy; and $R_4$ is 2 (R)-hydroxyindan-1(S)-yl, in free form or in pharmaceutically accepteable acid addition salt form.

2. A pharmaceutical composition comprising a compound of formula is as defined in claim 1 in free form or pharmaceutically acceptable acid addition salt form, together with at least one pharmaceutically acceptable carrier or diluent.

3. A method of treating retroviral diseases, which comprises administering to a subject in need of such treatment an effective amount of a compound of formula is as defined in claim 1 in free form or in pharmaceutically acceptable acid addition salt form.

4. A method of treating HIV, which comprises administering a therapeutically effective amount of a compound according to claim 1 in free form or in pharmaceutically acceptable acid addition salt form to a subject in need of said treatment.

5. 4(S)-(Benzyloxycarbonyl-L-tert-leucinoyl)amino-3(S)-hydroxy-2(R)-(4methoxybenzyl-amino)-5-phenyl-pentanoic acid 1(S)-amino-2(R)-hydroxyindan-amide, in free form or in pharmaceutically acceptable acid addition salt form.

* * * * *